United States Patent [19]

Tachikawa

[11] Patent Number: 5,446,180
[45] Date of Patent: Aug. 29, 1995

[54] COMPOUNDS CONTAINING 1-AZA-3-OXA-4-SILACYCLOHEX-1-ENYL GROUPS, AND TAUTOMERS OF SAID COMPOUNDS

[75] Inventor: Mamoru Tachikawa, Kanagawa, Japan

[73] Assignee: Dow Corning Asia Ltd., Tokyo, Japan

[21] Appl. No.: 357,829

[22] Filed: Dec. 16, 1994

[30] Foreign Application Priority Data

Dec. 28, 1993 [JP] Japan .................................. 5-338549
Dec. 28, 1993 [JP] Japan .................................. 5-338550
Dec. 28, 1993 [JP] Japan .................................. 5-338553

[51] Int. Cl.⁶ .............................................. C07F 7/10
[52] U.S. Cl. .................................... 556/408; 556/400; 556/419; 556/465; 528/32
[58] Field of Search ............... 556/408, 419, 400, 465; 528/32

[56] References Cited

U.S. PATENT DOCUMENTS

| | | | |
|---|---|---|---|
| 3,479,383 | 11/1969 | Klebe | 556/408 |
| 3,655,615 | 4/1972 | Bush et al. | 556/408 X |
| 3,677,977 | 7/1972 | Bush et al. | 556/408 X |
| 3,755,398 | 8/1973 | Bush | 556/408 |
| 4,794,192 | 12/1988 | Stein | 556/408 |

OTHER PUBLICATIONS

Platinum–Catalyzed Intramolecular Hydrosilation of Allylamines: Formation of 1–Aza–2–silocyclobutanes and application to Stereoselective Synthesis of 2-Amino Alcohols, J. Org. Chem., 1990, 55, 3438–3439.

*Primary Examiner*—Paul F. Shaver
*Attorney, Agent, or Firm*—Alexander Weitz

[57] ABSTRACT

Novel 1-aza-3-oxa-4-silacyclohex-1-ene compounds, and tautomers thereof, having utility as chemical modifiers or cross linkers for hydroxy-containing organic or inorganic substances are disclosed, said compounds being represented by the general formula (I)

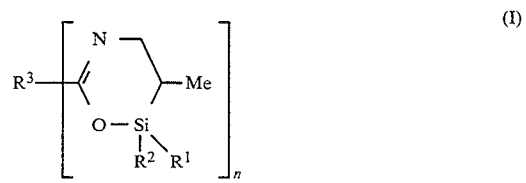

wherein $R^1$ and $R^2$ each independently denotes a monovalent organic group having 1 to 6 carbon atoms selected from the group consisting of saturated hydrocarbon groups and unsaturated hydrocarbon groups, $R^3$ deontes an organic group having 1 to 30 carbon atoms selected from the group consisting of saturated hydrocarbon groups and unsaturated hydrocarbon groups, said $R^3$ groups optionally containing a heteroatom selected from the group consisting of oxygen, nitrogen, sulfur, silicon, fluorine, chlorine, bromine and iodine, Me denotes a methyl radical and n is an integer having a value of 1 to 4.

11 Claims, No Drawings

COMPOUNDS CONTAINING 1-AZA-3-OXA-4-SILACYCLOHEX-1-ENYL GROUPS, AND TAUTOMERS OF SAID COMPOUNDS

FIELD OF THE INVENTION

The invention relates to compounds in which 1 to 4 1-aza-3-oxa-4-silacyclohex-1-enyl groups are each bonded through the imine carbon to a hydrocarbon group which can contain a heteroatom. The invention also relates to the tautomers of said compounds. The invention further relates to a method for modifying hydroxyl-containing organic substances and hydroxyl-containing inorganic substances using said compounds and tautomers thereof. Finally, the invention relates to a method for crosslinking two or more molecules of hydroxyl-containing polymer using the aforesaid compounds and tautomers thereof.

BACKGROUND OF THE INVENTION

Silicon compounds that contain 1-aza-3-oxa-4-silacyclohex-1-enyl groups within the individual molecule are heretofore unknown. While imine-bond containing O-silyl compounds occur in the form of the N,N-bis(trimethylsilyl)acetamides, these compounds are acyclic and contain only a single such functional group within the molecule.

One method for introducing an organoamide group onto hydroxyl or silanol consists of reaction with amide-functional silane coupling agent. Another method for accomplishing this derivatization consists of reacting a hydroxyl- or silanol-containing compound or solid with aminoalkyl-functional or chloroalkyl-functional silane coupling agent. In this method, the aminoalkyl-functional or chloroalkyl-functional silane coupling agent is first bonded on the hydroxyl group, and the organoamide group is then produced by further chemical modification of the aminoalkyl or chloroalkyl group. These methods suffer from the following three problems.

1. At present, only an extremely limited selection of amine-functional silane coupling agents is available commercially.

2. The reactions for converting aminoalkyl and chloroalkyl groups into an amide-functional group generate by-products and require severe conditions. This necessitates a by-product removal step and also risks chemical modification or decomposition of the modified target material.

3. The trialkyl-type silane coupling agents in general exhibit poor reactivities, which makes it extremely difficult to carry out the reaction with hydroxyl or silanol in an efficient or productive manner.

SUMMARY OF THE INVENTION

An object of the present invention is the introduction of novel 1-aza-3-oxa-4-silacyclohex-1-ene compounds and tautomers thereof which are capable of reacting with hydroxyl-containing organic and inorganic substances without the generation of by-products and through this reaction are able to modify or crosslink said organic or inorganic substance.

The characteristic feature of the 1-aza-3-oxa-4-silacyclohex-1-ene compounds of the present invention, and the feature on which these compounds differ substantially from previously known compounds, is that the six-member cyclic backbone contains a nitrogen-carbon double bond while the oxygen atom lying adjacent to this double bond is bonded to a silicon atom. As a result of this feature, the Si—O bond in this series of compounds readily undergoes hydrolysis with the formation of a chemically stable amide group.

Another object of the invention is the introduction of a method for modifying hydroxyl-containing organic and inorganic substances using the aforesaid 1-aza-3-oxa-4-silacyclohex-1-ene compounds and tautomers thereof.

An additional object of the invention is a method for crosslinking two or more molecules of hydroxyl-containing polymer using the aforesaid 1-aza-3-oxa-4-silacyclohex-1-ene compounds and tautomers thereof.

The instant invention has been described in Japanese Patent Applications Hei 5-338549, Hei 5-338550, and Hei 5-338553, the disclosures of which are hereby incorporated by reference.

DETAILED DESCRIPTION OF THE INVENTION

The invention comprises 1-aza-3-oxa-4-silacyclohex-1-ene compounds having the general formula (I) and tautomers thereof

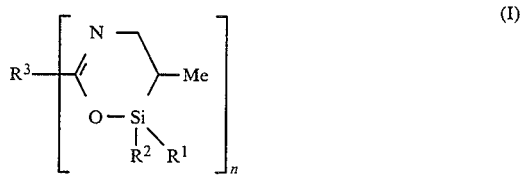

wherein $R^1$ and $R^2$ denote saturated or unsaturated $C_1$ to $C_6$ hydrocarbon groups which may be the same or different; $R^3$ denotes a monovalent to tetravalent saturated or unsaturated $C_1$ to $C_{10}$ hydrocarbon group, which may contain a heteroatom selected from nitrogen, oxygen, sulfur, silicon, fluorine, chlorine, bromine, or iodine; Me denotes a methyl group; and n is an integer with a value of 1 to 4. These definitions are maintained throughout the instant application.

$R^1$ and $R^9$ in the preceding formula represent saturated or unsaturated $C_1$ to $C_6$ hydrocarbon groups which may be the same or different, and preferably represent saturated or unsaturated $C_1$ to $C_3$ hydrocarbon groups which may be the same or different. $R^1$ and $R^2$ are exemplified by methyl, ethyl, propyl, butyl, pentyl, hexyl, vinyl, allyl, butenyl, pentenyl, hexenyl, and phenyl.

$R^3$ is specifically exemplified by monovalent radicals such as methyl, ethyl, vinyl, propyl, 3,3,3-trifluoropropyl, isopropyl, isopropenyl, allyl, n-butyl, isobutyl, sec-butyl, tert-butyl, butenyl, crotyl, n-pentyl, neopentyl, pentenyl, cyclopentyl, cyclopentenyl, n-hexyl, hexenyl, cyclohexyl, cyclohexenyl, heptyl, methylcyclohexyl, octyl, octenyl, cyclooctyl, phenyl, 4-chlorophenyl, 4-fluorophenyl, pentafluorophenyl, 4-bromophenyl, 4-vinylphenyl, 4-ethylphenyl, 4-dodecylphenyl, 4-trimethylsilylphenyl, 4-isopropenylphenyl, 4-cyanophenyl, 3-chlorophenyl, 3-fluorophenyl, 3-bromophenyl, 3-vinylphenyl, 3-ethylphenyl, 3-dodecylphenyl, 3-trimethylsilylphenyl, 3-isopropenylphenyl, 4-tolyl, 3-tolyl, 2-tolyl, and so forth.

The group $R^3$ is also exemplified by divalent radicals such as methylene, dimethylene, trimethylene, meta-phenylene, para-phenylene, para-tolylene, para-biphenylene, and so forth; by trivalent radicals such as methine, 1,3,5-phenenyl, and so forth; and by the di-, tri-, and tetravalent radicals with the following structures.

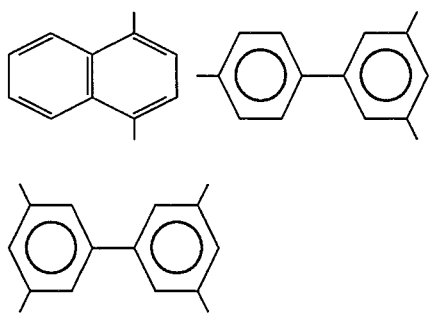

The group $R^3$ is preferably an aryl group, which may optionally contain a heteroatom as listed above, and $R^3$ preferably contains 1 to 18 carbons and more preferably 1 to 12 carbons.

Examples of tautomers of the 1-aza-3-oxa-4-silacyclohex-1-ene compounds (I) are obtained when at least one of the 1-aza-3-oxa-4-silacyclohex-1-enyl groups in (I) appears as the 1-acyl-1-aza-2-silacyclobutyl group with the formula (Ia) given below.

Compounds (I) according to the present invention are exemplified by
2,4,4,5-tetramethyl-1-aza-3-oxa-4-silacyclohex-1-ene,
2-ethyl-4,4,5-trimethyl-1-aza-3-oxa-4-silacyclohex-1-ene,
2-vinyl-4,4,5-trimethyl-1-aza-3-oxa-4-silacyclohex-1-ene,
2-propyl-4,4,5-trimethyl-1-aza-3-oxa-4-silacyclohex-1-ene,
2-isopropyl-4,4,5-trimethyl-1-aza-3-oxa-4-silacyclohex-1-ene,
2-propenyl-4,4,5-trimethyl-1-aza-3-oxa-4-silacyclohex-1-ene,
2-isopropenyl-4,4,5-trimethyl-1-aza-3-oxa-4-silacyclohex-1-ene,
2-allyl-4,4,5-trimethyl-1-aza-3-oxa-4-silacyclohex-1-ene,
2-butyl-4,4,5-trimethyl-1-aza-3-oxa-4-silacyclohex-1-ene,
2-tert-butyl-4,4,5-trimethyl-1-aza-3-oxa-4-silacyclohex-1-ene,
2-sec-butenyl-4,4,5-trimethyl-1-aza-3-oxa-4-silacyclohex-1-ene,
2-hexyl-4,4,5-trimethyl-1-aza-3-oxa-4-silacyclohex-1-ene,
2-hexenyl-4,4,5-trimethyl-1-aza-3-oxa-4-silacyclohex-1-ene,
2-cyclohexyl-4,4,5-trimethyl-1-aza-3-oxa-4-silacyclohex-1-ene,
2-phenyl-4,4,5-trimethyl-1-aza-3-oxa-4-silacyclohex-1-ene,
2-p-chlorophenyl-4,4,5-trimethyl-1-aza-3-oxa-4-silacyclohex-1-ene,
2-p-fluorophenyl-4,4,5-trimethyl-1-aza-3-oxa-4-silacyclohex-1-ene,
2-vinylphenyl-4,4,5trimethyl-1-aza-3-oxa-4-silacyclohex-1-ene,
2-pentafluorophenyl-4,4,5-trimethyl-1-aza-3-oxa-4-silacyclohex-1-ene,
2p-tolyl-4,4,5-trimethyl-1-aza-3-oxa-4-silacyclohex-1-ene,
2-m-tolyl-4,4,5-trimethyl-1-aza-3-oxa-4-silacyclohex-1-ene,
2-dodecylphenyl-4,4,5-trimethyl-1-aza-3-oxa-4-silacyclohex-1-ene,
2-naphthyl-4,4,5-trimethyl-1-aza-3-oxa-4silacyclohex-1-ene, and tautomers of the preceding.

Compounds with the following general formulas (II), (III), and (IV) and their tautomers are particularly preferred as the 1 aza-3-oxa-4-silacyclohex-1-ene compounds based on starting material availability.

wherein

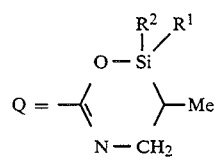

Compounds (I) and tautomers thereof can be synthesized from 1-aza-2-silacyclobutane compounds with general formula (V)

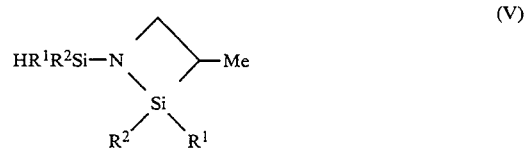

and carbonyl compounds with general formula (VI)

wherein X hereinafter represents chlorine, bromine, or the acyloxy group $OC(=O)R^4$; and $R^4$ hereinafter denotes a saturated or unsaturated $C_1$ to $C_{30}$ hydrocarbon group, which may contain a heteroelement selected from nitrogen, oxygen, sulfur, silicon, fluorine, chlorine, bromine, or iodine, by a reaction in which the compound $HR^1R^2SiX$ is also produced. $R^4$ is specifically exemplified by monovalent radicals such as methyl, ethyl, vinyl, propyl, 3,3,3-trifluoropropyl, isopropyl, isopropenyl, allyl, n-butyl, isobutyl, sec-butyl, tert-butyl, butenyl, crotyl, n-pentyl, neopentyl, pentenyl, cyclopentyl, cyclopentenyl, n-hexyl, hexenyl, cyclohexyl, cyclohexenyl, heptyl, methylcyclohexyl, octyl, octenyl, cyclooctyl, phenyl, 4-chlorophenyl, 4-fluorophenyl, pentafluorophenyl, 4-bromophenyl, 4-vinylphenyl, 4-ethylphenyl, 4-dodecylphenyl, 4-trimethylsilylphenyl, 4-isopropenylphenyl, 4-cyanophenyl, 3-chlorophenyl, 3-fluorophenyl, 3-bromophenyl, 3-vinylphenyl, 3-ethylphenyl, 3-dodecylphenyl, 3-trimethylsilylphenyl, 3-isopropenylphenyl, p-tolyl, m-tolyl, o-tolyl, and so forth.

Compound (I) can be produced by simply mixing compounds (V) and (VI) in the presence or absence of solvent. Reaction temperatures of $-20°$ C. to $150°$ C. can be used. Aprotic organic solvents can be used as the solvent for this reaction, for example, ethers such as diethyl ether, tetrahydrofuran, and so forth; saturated hydrocarbons such as butane, pentane, hexane, heptane, octane, cyclohexane, methylcyclohexane, and so forth; unsaturated hydrocarbons such as butene, pentene, hexene, octene, cyclohexene, and so forth; aromatic hydrocarbons such as benzene, toluene, xylene, ethylbenzene, and so forth; and halogenated hydrocarbons such as dichloromethane, chloroform, carbon tetrachloride, trichloroethane, chlorobenzene, and so forth.

Compound (V) is specifically exemplified by
1-dimethylsilyl-2,2,3-trimethyl-1-aza-2-silacyclobutane,
1-diethylsilyl-2,2-diethyl-3-methyl-1-aza-2-silacyclobutane,
1-dipropylsilyl-2,2-dipropyl-3-methyl-1-aza-2-silacyclobutane,
1-diphenylsilyl-2,2-diphenyl-3-methyl-1-aza-2-silacyclobutane,
1-methylethylsilyl-2-ethyl-2,3-dimethyl-1-aza-2-silacyclobutane,
1-methylphenylsilyl-2-phenyl-2,3-dimethyl-1-aza-2-silacyclobutane, and so forth.

Compound (VI) is specifically exemplified by acetyl chloride, propionyl chloride, acryloyl chloride, methacryloyl chloride, isobutyryl chloride, butyryl chloride, pivaloyl chloride, valeryl chloride, stearoyl chloride, benzoyl chloride, toluoyl chloride, p-chlorobenzoyl chloride, p-vinylbenzoyl chloride, p-dodecylbenzoyl chloride, naphthoyl chloride, acetyl bromide, acryloyl bromide, methacryloyl bromide, benzoyl bromide, toluoyl bromide, p-vinylbenzoyl bromide, naphthoyl bromide, acetyl iodide, acryloyl iodide, methacryloyl iodide, benzoyl iodide, acetic anhydride, acrylic anhydride, methacrylic anhydride, propionic anhydride, benzoic anhydride, p-chlorobenzoic anhydride, and so forth.

Compound (VI) is also specifically exemplified by malonyl dichloride, succinyl dichloride, glutaryl dichloride, adipoyl dichloride, phthaloyl dichloride, isophthaloyl dichloride, terephthaloyl dichloride, trimesoyl chloride, malonyl dibromide, succinyl dibromide, glutaryl dibromide, adipoyl dibromide, phthaloyl dibromide, isophthaloyl dibromide, terephthaloyl dibromide, trimesoyl bromide, and acid halides with the following structures.

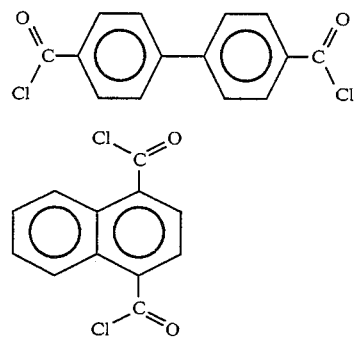

Another aspect of the present invention comprises a method for introducing an amide group onto a hydroxyl group by reacting the 1-aza-3-oxa-4-silacyclohex-1-ene compound (I) or tautomer thereof with a hydroxyl-containing inorganic substance or a hydroxyl-containing organic substance as indicated by the equation (i) wherein B represents the main body of the hydroxyl-containing inorganic substance or hydroxyl-containing organic substance. This reaction can be run at ambient temperature and pressure.

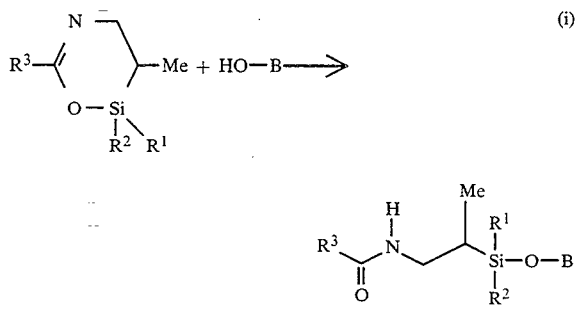

Preferred embodiments of the hydroxyl-containing inorganic substance and hydroxyl-containing organic substance used in this mode are silanol-containing organic compounds, silanol-containing polymers, and silanol-containing inorganic solids. In the case of these substances, an amide group that is chemically bonded across a siloxane linkage can be introduced through the following reaction.

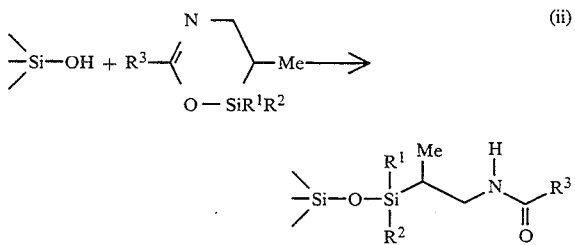

Other preferred functional groups include the structures

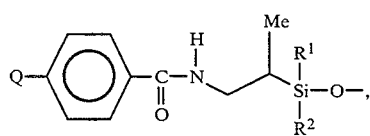

-continued

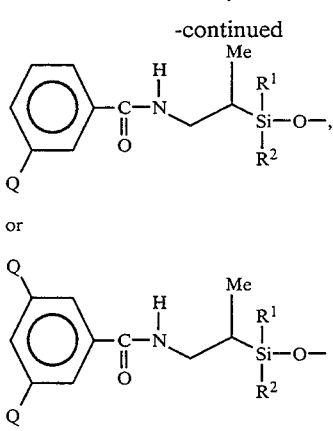

or

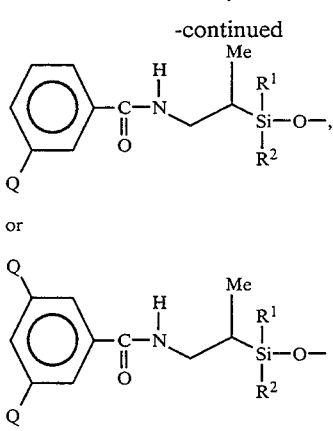

wherein Q is defined as above, and the corresponding tautomeric functional groups, may be introduced into hydroxyl-containing organic and inorganic substances by the reaction of a hydroxyl-containing organic or inorganic substance with a compound having formula (II), (III), or (IV) or tautomer thereof. This reaction can generally be run by mixing hydroxyl-containing organic or inorganic substance residing at ambient temperature with, e.g., a compound (II), (III), or (IV), or tautomer thereof, also residing at ambient temperature. This reaction is generally run at ambient pressure, and compound (II), (III), or (IV) or tautomer should be used in an at least equimolar quantity based on the hydroxyl group in the hydroxyl-containing organic or inorganic substance.

Subject hydroxyl-containing organics are exemplified by alcohols such as methanol, ethanol, propyl alcohol, isopropyl alcohol, n-butyl alcohol, tert-butyl alcohol, cyclohexyl alcohol, triphenylmethanol, ethylene glycol, and propylene glycol; by aromatic hydroxylic compounds such as phenol, cresol, xylenol, naphthol, and resorcinol; by carboxylic acids such as formic acid, acetic acid, chloroacetic acid, trifluoroacetic acid, propionic acid, benzoic acid, acrylic acid, methacrylic acid, malonic acid, adipic acid, and terephthalic acid; by polymers such as polyvinyl alcohol; by SiOH-containing organic compounds, i.e., silanols such as trimethylsilanol, triphenylsilanol, diphenylsilanediol, and so forth; and also by high molecular weight silicon compounds such as silanol-endblocked polydimethylsiloxanes and silanol-functional silicone resins. The hydroxyl-bearing inorganics are exemplified by metals which carry a surface coating of oxide, such as iron, zinc, titanium, etc., and by the alloys of such metals; by metal oxides such as iron oxide, zinc oxide, titania, zirconia, and so forth; by the surface of silicon and metallosilicons such as ferrosilicon; and by silicon oxides such as silica and silica-titania. Particularly preferred among the preceding are silanol-containing organic compounds, silanol-containing polymers, and silanol-containing inorganic substances.

Products obtained as described above may be further reacted and thereby bonded with additional hydroxyl-bearing substance, or crosslinkages can be produced within the product itself by exposure to moisture. In the later case, the water behaves like a dihydroxy compound.

Another preferred embodiment of the invention comprises the crosslinking of a hydroxyl-containing organic or inorganic substance through its reaction, in the presence or absence of water, with a compound (II), (III), or (IV) or tautomer thereof. The organic and inorganic substances usable in this embodiment are exemplified by the organic and inorganic substances listed above. Silanol-containing organic compounds, silanol-containing polymers, and silanol-containing inorganic substances are again preferred.

The silanol-containing organic compounds are exemplified by silanols such as trimethylsilanol and diphenylsilanediol, and said silanol-containing polymers are exemplified by silanol-functional silicones, silanol-containing silicone-modified organic polymers, silanol-functional compounds that are composed of the silicon functional groups given below, and polymer resins that carry surface silanol. R in the following formulas represents $C_1$ to $C_6$ saturated or unsaturated hydrocarbon groups, which may contain a heteroatom selected from nitrogen, oxygen, sulfur, silicon, fluorine, chlorine, bromine, and iodine.

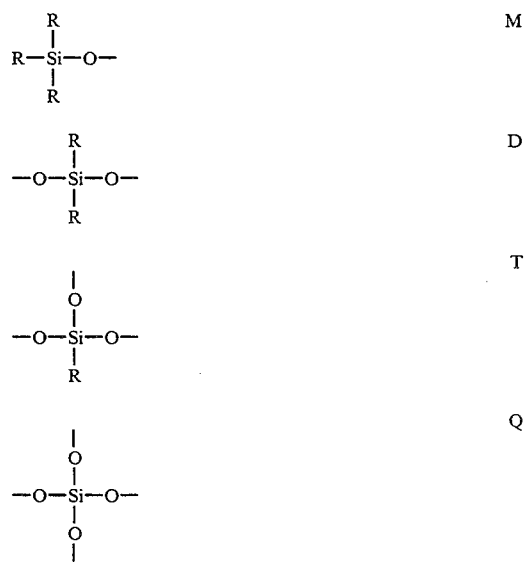

The silanol-containing inorganic substances are exemplified by oxides such as quartz, aerosil, silica, zeolites, kaolin, silica-titania, and glass, and also by silicon and silicon alloys whose surface is coated with an oxide or silanol group film.

Compounds (I) according to the present invention carry 1 to 4 azaoxasilacyclohexenyl groups bonded into a single unit through imide carbons. When said compounds (I) or tautomers thereof are brought into contact with a hydroxyl-containing compound, hydroxyl-containing polymer, or hydroxyl-containing solid, the azaoxasilacyclohexenyl group reacts with the hydroxyl group, which makes possible the introduction, without the generation of free reaction by-products, of chemical bond crosslinkages between individual molecules of the compound or polymer or between particles of the solid. When compound (I) or tautomer thereof is used in larger quantities than would be required by the aforesaid crosslinking reaction, unreacted azaoxasilacyclohexenyl groups will initially remain present bonded to the polymer or solid, and this makes possible the formation of crosslinkages in the polymer or solid by reaction with water molecules present in the ambient gas phase. The following are characteristic features of methods that use the compounds (I) and tautomers thereof proposed by the present invention.

(1) High reactivity; a rapid and complete modification or crosslinking reaction.

(2) No risk of spurious reactions by by-products since no by-products are products are produced by the modification or crosslinking reaction. Also, no requirement for a process step devoted to the elimination of by-products, which may be flammable, toxic, or foul-smelling.

EXAMPLES

The invention is explained in greater detail below through working examples, but the invention is not thereby limited. 1-aza-3-oxa-4-silacyclohex-1-enyl is abbreviated as azaoxasilacyclohexenyl in the examples.

In the product characterization data reported in the examples, $^1$H NMR refers to proton nuclear magnetic resonance spectroscopy, $^{13}$C (1H) NMR refers to proton-decoupled $^{13}$C nuclear magnetic resonance spectroscopy, and $^{29}$Si (1H) NMR refers to proton-decoupled $^{29}$Si nuclear magnetic resonance spectroscopy. CDCl$_3$ refers to deuterochloroform. In the proton nuclear magnetic resonance spectroscopic data, the s, d, t, m, and br reported in parentheses indicate, respectively, singlet, doublet, triplet, multiplet, and broad. 1H, 2H, 3H, etc., refer, respectively, to a signal strength corresponding to 1 proton, 2 protons, 3 protons, etc. The chemical shifts in the nuclear magnetic resonance spectra are in all cases reported using 0 ppm for tetramethylsilane. GC-MS refers to gas chromatography-mass spectrometric analysis, and GPC refers to gel permeation chromatography.

REFERENCE EXAMPLE 1

Synthesis of 1-dimethylsilyl-2,2,3-trimethyl-1-aza-2-silacyclobutane

First Step: Synthesis of N,N-bis(dimethylsilyl)allylamine

The following were placed in a 1-liter three-neck flask equipped with mechanical stirrer, addition funnel, and water-cooled condenser: 400 mL hexane, 100 g triethylamine, and 40 g allylamine. 60 g dimethylchlorosilane was then added dropwise over 30 minutes. The resulting slurry, which contained a large amount of precipitate, was heated for 8 hours at approximately 60° C. while stirring slowly, and the precipitate was then removed by filtration. The precipitate was washed with 300 mL hexane, and the filtrates were combined. The hexane was removed by simple distillation, and N,N-bis(dimethylsilyl)allylamine was then recovered in a yield of 85% by distillation.

Second Step: Synthesis of 1-dimethylsilyl-2,2,3-trimethyl-1-aza-2-silacyclobutane Into a 500-mL roundbottom flask were introduced 100 mL N,N-bis(dimethylsilyl)allylamine and 100 mL toluene and then 5 mg bis(triphenylphosphine)platinum dichloride (PtCl$_2$(PPh$_3$)$_2$). The reaction was heated for 1 hour at 80° C., and the reaction product was isolated and purified by distillation.

Analysis dimethylsilyl 1-2,2,3-trimethyl-1-aza-2-silacyclobutane $^1$H NMR (d-chloroform): 0.18 ppm (3H, s), 0.21 ppm (3H, s), 1.11 ppm (3H, d, J=7.6 Hz), 1.59 ppm (1H, m), 2.83 ppm (1H, dd, J=6.5 Hz, J'=4.7 Hz), 3.19 ppm (2H, d, J=6.0 Hz), 3.54 ppm (1H, dd, J=8.5 Hz, J'=6.5 Hz), 4.99 ppm (1H, dd, J =10.1 Hz, J'=1.7 Hz), 5.08 ppm (1H, dd, J=17.1 Hz, J'=1.7 Hz), 5.75 ppm (1H, ddt, J=17.1 Hz, J'=10.1 Hz, J''=6.0 Hz).

$^{13}$C (1H) NMR (d-chloroform): −1.6 ppm, 1.7 ppm, 14.9 ppm, 18.6 ppm, 51.0 ppm, 57.9 ppm, 115.0 ppm, 137.4 ppm.

$^{29}$Si (1H) NMR (d-chloroform): 25.4 ppm (m) mass spectrum: m/z =155, 140, 126, 112, 98, 86, 87, 85, 59, 58.

This compound has been previously reported in the literature (K. Tamao, Y. Nakagawa, and Y. Ito, J. Org. Chem., 19 90, 55, 3438).

EXAMPLE 1

Synthesis of 2,4,4,5-tetramethyl-1-aza-3-oxa-4-silacyclohex-1-ene 2 parts 1-dimethylsilyl-2,2,3-trimethyl-1-aza-2-silacyclobutane and 5 parts chloroform were placed in a nitrogen-purged container, to which a mixture of 2 parts chloroform and 1 part acetic anhydride was added dropwise over 10 minutes. The mixture was then heated for 5 hours at 70° C. on an oil bath. Analysis by gas chromatography and GC-MS indicated the complete absence of the starting 1-dimethylsilyl-2,2,3-trimethyl-1-aza-2-silacyclobutane and confirmed the production of (HMe$_2$Si)$_2$NCH$_2$CHMeSiMe$_2$OAc and 2,4,4,5-tetramethyl-1-aza-3-oxa-4-silacyclohex-1-ene in addition to other products.

Results of Mass Spectrometric Analysis

For (HMe$_2$Si)$_2$NCH$_2$CHMeSiMe$_2$OAc (EI, m/z (relative intensity)): 59 (22.0), 73 (7.8), 75 (16.6), 86 (24.9), 146 (100), 190 (9.2), 192 (4.9), 204 (1.7), 206 (2.1), 232 (1.2), 234 (0.6), 276 (0.5), 290 (0.6), 291 (0.3).

For 2,4,4,5-tetramethyl-1-aza-3-oxa-4-silacyclohex-1-ene (EI, m/z (relative intensity)): 58 (68.1), 59 (44.9), 75 (100), 86 (22.7), 100 (27.1), 142 (23.1), 156 (27.8), 157 (35.0)

EXAMPLE 2

Synthesis of 2-vinyl-4,4,5-trimethyl-1-aza-3-oxa-4-silacyclohex-1-ene 2 parts 1-dimethylsilyl-2,2,3-trimethyl-1-aza-2-silacyclobutane and 5 parts ether were placed in a nitrogen-purged container, to which a mixture of 2 parts ether and 1 part acryloyl chloride was added dropwise over 10 minutes. The reaction mixture was allowed to stand overnight at room temperature. Analysis by gas chromatography indicated the complete absence of the starting 1-dimethylsilyl-2,2,3-trimethyl-1-aza-2-silacyclobutane, while dimethylchlorosilane, (HMe$_2$Si)$_2$NCH$_2$CHMeSiMe$_2$Cl, and 2-vinyl-4,4,5-trimethyl-1-aza-3-oxa-4-silacyclohex-1-ene were detected as principal products.

Results of Mass Spectrometric Analysis

For (HMe$_2$Si)$_2$NCH$_2$CHMeSiMe$_2$Cl (EI, m/z (relative intensity)): 59 (25.4), 86 (35.8), 146 (100), 210 (4.5), 212 (2.0), 224 (1.4), 226 (0.6).

For 2-vinyl-4,4,5-trimethyl-1-aza-3-oxa-4-silacyclohex-1-ene (EI, m/z (relative intensity)): 54 (38.9), 58 (47.3), 59 (46.3), 75 (60.3), 86 (27.0), 94 (18.2), 112 (14.7), 154 (100), 168 (98.9), 169 (53.1), 170 (10.2).

EXAMPLE 3

Synthesis of 2-isopropenyl-4,4,5-trimethyl-1-aza-3-oxa-4-silacyclohex-1-ene 2 parts 1-dimethylsilyl-2,2,3-trimethyl-1-aza-2-silacyclobutane and 5 parts ether were placed in a nitrogen-purged container, to which a mixture of 2 parts ether and 1 part methacryloyl chloride was added dropwise over 10 minutes. The reaction mixture was allowed to stand overnight at room temperature. Analysis by gas chromatography indicated the complete absence of the starting 1-dimethylsilyl-2,2,3-trimethyl-1-aza-2-silacyclobutane, while dimethylchlorosilane, $(HMe_2Si)_2NCH_2CHMeSiMe_2Cl$, and 2-isopropenyl-4,4,5-trimethyl-1-aza-3-oxa-4-silacyclohex-1-ene were detected as principal products. The 2-isopropenyl-4,4,5-trimethyl-1-aza-3-oxa-4-silacyclohex-1-ene was isolated from the reaction mixture by vacuum distillation.

RESULTS OF ANALYSIS 2-isopropenyl-4,4,5-trimethyl-1-aza-3-oxa-4-silacyclohex-1-ene $^1H$ NMR (CDCl$_3$, ppm): 0.15 (3H, s), 0.17 (3H, s), 0.95 (3H, d), 1.0 (1H, m), 1.85 (3H, s), 3.2 (1H, dd), 3.54 (1H, dd), 5.2 (1H, s), 5.7 (1H, s).

$^{13}C$ {$^1H$} NMR (CDCl$_3$, ppm): −3.99, −0.97, 12.15, 16.20, 19.17, 50.12, 118.62, 139.67, 157.14.

$^{29}Si$ {$^1H$} NMR (CDCl$_3$, ppm): 21.95.

mass spectrometric analysis (EI, m/z (relative intensity)): 58 (38.8), 59 (6.7), 75 (97.3), 108 (15.1), 126 (21.1), 141 (32.8), 168 (100), 182 (78.9), 183 (98.4), 184 (17.8).

EXAMPLE 4

Synthesis of 2-phenyl-4,4,5-trimethyl-1-aza-3-oxa-4-silacyclohex-1-ene 2 parts 1-dimethylsilyl-2,2,3-trimethyl-1-aza-2-silacyclobutane and 5 parts ether were placed in a nitrogen-purged container, to which a mixture of 2 parts ether and 1 part benzoyl chloride was added dropwise over 10 minutes. The reaction mixture was allowed to stand overnight at room temperature. Analysis by gas chromatography indicated the complete absence of the starting 1-dimethylsilyl-2,2,3-trimethyl-1-aza-2-silacyclobutane, while dimethylchlorosilane, $(HMe_2Si)_2NCH_2CHMeSiMe_2Cl$, and 2-phenyl-4,4,5-trimethyl-1-aza-3-oxa-4-silacyclohex-1-ene were detected as principal products. The 2-phenyl-4,4,5-trimethyl-1-aza-3-oxa-4-silacyclohex-1-ene was isolated from the reaction mixture by vacuum distillation.

RESULTS OF ANALYSIS 2-phenyl-4,4,5-trimethyl-1-aza-3-oxa-4-silacyclohex-1-ene $^1H$ NMR (CDCl$_3$, ppm): 0.41 (3H, s), 0.43 (3H, s), 1.13 (3H, d), 1.14 (1H, m), 3.54 (1H, dd), 3.84 (1H, dd), 7.4–8.1 (5H, m).

$^{13}C$ {$^1H$} NMR (CDCl$_3$, ppm): −3.92, −1.37, 12.10, 16.06, 49.94, 127.21, 127.74, 130.00, 134.90, 155.66.

$^{29}Si$ {$^1H$} NMR (CDCl$_3$, ppm): 22.89.

mass spectrometric analysis (EI mode, 70 eV), m/z (relative intensity)=219 (26), 218 (100), 105 (15), 104 (19), 77 (21), 75 (21), 59 (22), 58 (19).

EXAMPLE 5

Synthesis of 2-p-chlorophenyl-4,4,5-trimethyl-1-aza-3-oxa-4-silacyclohex-1-ene 2 parts 1-dimethylsilyl-2,2,3-trimethyl-1-aza-2-silacyclobutane and 5 parts ether were placed in a nitrogen-purged container, to which a mixture of 2 parts ether and 1 part p-chlorobenzoyl chloride was added dropwise over 10 minutes. The reaction mixture was allowed to stand overnight at room temperature. Analysis by gas chromatography indicated the complete absence of the starting 1-dimethylsilyl-2,2,3-trimethyl-1-aza-2-silacyclobutane, while dimethylchlorosilane and 2-p-chlorophenyl-4,4,5-trimethyl-1-aza-3-oxa-4-silacyclohex-1-ene were detected as principal products. The 2-p-chlorophenyl-4,4,5-trimethyl-1-aza-3-oxa-4-silacyclohex-1-ene was isolated from the reaction mixture by vacuum distillation.

Results of Analysis 2-p-chlorophenyl-4,4,5-trimethyl-1-aza-3-oxa-4-silacyclohex-1-ene $^1H$ NMR (CDCl$_3$, ppm): 0.31 (3H, s), 0.34 (3H, s), 1.02 (3H, d), 1.08 (1H, m), 3.41 (1H, dd, 14.7 Hz, 8.8 Hz), 3.75 (1H, dd, 14.7 Hz, 4.2 Hz), 7.31 (2H, m), 7.87 (2H, m).

$^{13}C$ {$^1H$} NMR (CDCl$_3$, ppm): −3.87, −1.32, 12.10, 15.96, 50.13, 128.01 (2C), 128.70 (2C), 133.55, 136.15, 154.67.

$^{29}Si$ {$^1H$} NMR (CDCl$_3$, ppm): 23.18.

mass spectrometric analysis (EI, 70 eV), m/z (relative intensity=254 (41), 253 (29), 252 (100), 139 (15), 138 (14), 111 (12), 75 (32), 59 (24), 58 (32), 57 (22).

EXAMPLE 6

Synthesis of 2-tert-butyl-4,4,5-trimethyl-1-aza-3-oxa-4-silacyclohex-1-ene 2 parts 1-dimethylsilyl-2,2,3-trimethyl-1-aza-2-silacyclobutane and 5 parts ether were placed in a nitrogen-purged container, to which a mixture of 2 parts ether and 1 part trimethylacetyl chloride was added dropwise over 10 minutes. The reaction mixture was allowed to stand overnight at room temperature. Analysis by gas chromatography indicated the complete absence of the starting 1-dimethylsilyl-2,2,3-trimethyl-1-aza-2-silacyclobutane, while dimethylchlorosilane, $(ClMe_2Si)_2NCH_2CHMeSiMe_2Cl$, and 2-tert-butyl-4,4,5-trimethyl-1-aza-3-oxa-4-silacyclohex-1-ene were detected as principal products.

RESULTS OF ANALYSIS 2-tert-butyl-4,4,5-trimethyl-1-aza-3-oxa-4-silacyclohex-1-ene mass spectrometric analysis (EI, 70 eV), m/z (relative intensity)=199 (25), 198 (21), 184 (100), 157 (36), 156 (12), 143 (25), 142 (71), 100 (34), 86 (18), 85 (23), 75 (61), 61 (11), 59 (35), 58 (28), 57 (31).

EXAMPLE 7

Synthesis of 1,4-bis(1-aza-3-oxa-4-silacyclohex-1-enyl)benzene 2 parts 1-dimethylsilyl-2,2,3-trimethyl-1-aza-2-silacyclobutane and 5 parts ether were placed in a nitrogen-purged container, to which a mixture of 2 parts ether and 1 part terephthaloyl dichloride was added dropwise over 10 minutes. The reaction mixture was allowed to stand overnight at room temperature. Analysis by NMR indicated the complete absence of the starting terephthaloyl dichloride, while dimethylchlorosilane, (HMe$_2$Si)$_2$NCH$_2$CHMeSiMe$_2$Cl, bis(1-aza-3-oxa-4-silacyclohex-1-enyl)benzene, and unreacted 1-dimethylsilyl-2,2,3-trimethyl-1-aza-2-silacyclobutane were detected as principal components. The components other than the bis(1-aza-3-oxa-4-silacyclohex-1-enyl)benzene were removed by heating under reduced pressure.

RESULTS OF ANALYSIS 1,4-bis(1-aza-3-oxa-4-silacyclohex-1-enyl)benzene $^1$H NMR (CDCl$_3$, ppm): 0.28 (3H, s), 0.32 (3H, s), 1.0 (3H, d), 1.05 (1H, m), 3.4 (1H, dd), 3.7 (1H, dd), 7.95 (2H, s).

$^{13}$C (1H) NMR (CDCl$_3$, ppm): −3.8, −1.3, 12.2, 16.1, 50.3, 127.0, 136.7, 155.4.

$^{29}$Si (1H) NMR (CDCl$_3$, ppm): 22.7.

EXAMPLE 8

Synthesis of 1,3,5-tris(1-aza-3-oxa-4-silacyclohex-1-enyl)benzene 2 parts 1-dimethylsilyl-2,2,3-trimethyl-1-aza-2-silacyclobutane and 5 parts ether were placed in a nitrogen-purged container, to which a mixture of 2 parts ether and 1 part trimesoyl chloride was added dropwise over 10 minutes. The reaction mixture was allowed to stand overnight at room temperature. Analysis by NMR indicated the complete absence of the starting trimesoyl chloride, while dimethylchlorosilane, (HMe$_2$Si)$_2$NCH$_2$CHMeSiMe$_2$Cl, 1,3,5-tris(1-aza-3-oxa-4-silacyclohex-1-enyl)benzene, and unreacted 1-dimethylsilyl-2,2,3-trimethyl-1-aza-2-silacyclobutane were detected as principal components. The components other than the 1,3,5-tris(1-aza-3-oxa-4-silacyclohex-1-enyl)benzene were removed by heating under reduced pressure.

RESULTS OF ANALYSIS 1,3,5-tris(1-aza-3-oxa-4-silacyclohex-1-enyl)benzene $^1$H NMR (CDCl$_3$, ppm): 0.3 (3H, s), 0.35 (3H, s), 1.0 (3H, d), 1.0–1.05 (1H, m), 3.4 (1H, dd), 3.7 (1H, dd), 8.4 (1H, s).

$^{13}$C (1H) NMR (CDCl$_3$, ppm): −3.7, −1.2, 12.3, 16.0, 50.4, 128.2, 135.2, 155.2.

$^{29}$Si (1H) NMR (CDCl$_3$, ppm): 22.6.

EXAMPLE 9

Reaction between Methanol and 2-isopropenyl-4,4,5-trimethyl-1-aza-3-oxa-4-silacyclohex-1-ene The addition of 2 parts methanol to 1 part 2-isopropenyl-4,4,5-trimethyl-1-aza-3-oxa-4-silacyclohex-1-ene resulted in the instantaneous evolution of heat and completion of the reaction. Removal of methanol by stirring the reaction mixture in a vacuum for 1 hour at room temperature yielded the essentially pure methanol adduct, N-[2-(dimethylmethoxysilyl)propyl]methacrylamide.

RESULTS OF ANALYSIS $^1$H NMR (CDCl$_3$, ppm): 0.06 (6H, s), 0.89 (3H, d), 1.00 (1H, m), 1.88 (3H, s), 3.10 (1H, m), 3.30 (1H, m), 3.36 (3H, s), 5.21 (1H, s), 5.60 (1H, s).

$^{29}$Si {1H} NMR (CDCl$_3$, ppm): 21.9.

mass spectrometric analysis: m/z (relative intensity)=215 (6.2), 214 (5.2), 201 (23), 200 (18), 183 (10), 182 (11), 168 (24), 159 (23), 158 (21), 142 (10), 115 (20), 92 (35), 91 (39), 90 (14), 89 (100), 75 (24), 69 (46), 61 (14), 59 (79).

EXAMPLE 10

Reaction Between Polysiloxanediol and 2-isopropenyl-4,4,5-trimethyl-1-aza-3-oxa-4-silacyclohex-1-ene 4.5 parts silanol-endblocked polydimethylsiloxane with a molecular weight (M$_n$) of approximately 1600 was added to a solution of 10 parts chloroform and 1 part 2-isopropenyl-4,4,5-trimethyl-1-aza-3-oxa-4-silacyclohex-1-ene. Heat was immediately evolved from the mixture, and the reaction was complete within 1 minute.

RESULTS OF ANALYSIS $^1$H NMR (CDCl$_3$, ppm): −0.1 −0.2 (104H, m), 0.95 (4H, m), 1.9 (3H, s), 3.1–3.4 (2H, m), 5.2 (1H, s), 5.6 (1H, s), 6.3 (1H, br).

The molecular weight (Mn) of the polysiloxane prior to the reaction was 1600 as measured by gel permeation chromatography (GPC). Its molecular weight was 1760 after the reaction.

EXAMPLE 11

Reaction Between Tetrasiloxaneol and 2-phenyl-4,4,5-trimethyl-1aza-3-oxa-4-silacyclohex-1-ene 1.4 parts nonamethyltetrasiloxane-1-ol was added at ambient temperature to a solution of 1 part 2-phenyl-4,4,5-trimethyl-1-aza-3-oxa-4-silacyclohex-1-ene in 5 parts toluene. A reaction occurred immediately to produce the amide-modified siloxane.

RESULTS OF ANALYSIS $^1$H NMR (CDCl$_3$, ppm): 0–0.05 (33H, m), 100 (3H, d), 1.08 (1H, m), 3.35 (1H, m), 3.50 (1H, m), 7.0 (1H, br), 7.2–7.8 (5H, m).

$^{13}$C {1H} (CDCl$_3$, ppm): −1.70, −1.47, 0.81, 089, 0.92, 1.53, 11.86, 22.20, 42.16, 126.83, 128.08, 130.82, 134.72, 167.54.

$^{29}$Si {1H} NMR (CDCl$_3$, ppm): −22.06, −21.42, −20.42, 7.29, 9.02.

EXAMPLE 12

Reaction Between Methanol and 2-phenyl-4,4,5-trimethyl-1aza-3-oxa-4-silacyclohex-1-ene 0.15 part methanol was added at ambient temperature to a solution of 1 part 2-phenyl-4,4,5-trimethyl-1-aza-3-oxa-4-silacyclohex-1-ene in 5 parts toluene. A reaction occurred immediately with the production of the amide-functional methoxysilane as sole product.

RESULTS OF ANALYSIS $^1$H NMR (CDCl$_3$, ppm): 0.14 (3H, 0.16 (3H), 1.01 (3H, d) 1.16(1H, m), 3.46 (3H, s), 3.48 (1H, m), 3.51 (1H, m), 7.34–7.83 (6H, m). $^{13}$C {1H} NMR (CDCl$_3$, ppm): −5.2, −4.2, 11.92, 20.48, 42.39, 50.28, 126.64, 128.11, 130.86, 134.53, 167.08. $^{29}$Si {1H} NMR (CDCl$_3$, ppm): 22.16.

EXAMPLE 13

Reaction Between Silica and 2-phenyl-4,4,5-trimethyl-1-aza-3-oxa-4-silacyclohex-1-ene A slurry was prepared by adding 1.1 parts toluene to 1 part Wakogel C-200 silica (dried 24 hours at 100° C.) The addition of 0.5 part 2-phenyl-4,4,5-trimethyl-1-aza-3-oxa-4-silacyclohex-1-ene (synthesized as in Example 4) to the slurry resulted in the immediate evolution of heat. The slurry was allowed to stand for 30 minutes, and the silica was then separated by filtration. The recovered silica was first washed 5 times with a 1:1 mixture of toluene-hexane and was then washed 5 times with hexane. 1.28 parts of a modified silica was obtained by eliminating the hexane by air drying and drying overnight at 100° C. The infrared absorption spectrum of the modified silica was compared with the IR spectrum of the silica prior to its modification, and strong absorptions were found to occur at 3304 cm$^{-1}$ (N—H); 3064 cm$^{-1}$, 2959 cm$^{-1}$, and 2872 cm$^{-1}$ (C—H); 1640 cm$^{-1}$ (C=O); and 1545 cm$^{-1}$ (amide II). This confirmed that surface-bonded amide had been produced by the reaction of the silanol groups on the silica with the specified 1-aza-3-oxa-4-silacyclohex-1-ene compound.

EXAMPLE 14

Reaction of 1,4-bis(azaoxasilacyclohexenyl)benzene and nonamethyltetrasiloxane-1-ol 1.7 parts nonamethyltetrasiloxane-1-ol was added to 1 part 1,4-bis(azaoxasilacyclohexenyl)benzene dissolved in 10 parts tetrahydrofuran, and the reaction was stirred for 10 minutes. Removal of the tetrahydrofuran in a vacuum gave a white paste. The NMR spectrum was obtained by dissolving the residue in d-chloroform. The silanol group signal was no longer present in the $^1$H NMR spectrum, while the amide N—H proton had appeared.

RESULTS OF ANALYSIS

For the adduct of nonamethyltetrasiloxane-1-ol to 1,4-bis(1-aza-3-oxa-4-silacyclohex-1-enyl)benzene $^1$H NMR (CDCl$_3$, ppm): 0.01–0.06 (54H, m), 0.12 (3H, s), 0.13 (3H, s), 1.01 (6H, d), 1.05 (2H, m), 3.45 (2H, m), 3.53 (2H, m), 6.35 (2H, 1), 7.78 (4H, s).

$^{13}$C ($^1$H) NMR (CDCl$_3$, ppm): −1.6, −1.1, 1.0, 1.08, 1.14, 1.7. 12.1, 22.4, 42.6, 127.0, 137.3, 166.6.

Si ($^1$H) NMR (CDCl$_3$, ppm): −21.9, −21.4, −20.0, 7.4, 9.2.

EXAMPLE 15

Reaction of 1,4-bis(azaoxasilacyclohexenyl)benzene and alpha,omega-polysiloxanediol 4.5 parts alpha,omega-polydimethylsiloxanediol (number-average molecular weight M$_n$=1,590) was added to 1 part 1,4-bis(azaoxasilacyclohexenyl)benzene dissolved in 10 parts tetrahydrofuran, and the reaction was stirred for 10 minutes. The tetrahydrofuran was then removed in a vacuum, and the residue was dissolved in toluene and analyzed by GPC. The starting alpha,omega-polydimethylsiloxanediol had M$_n$=1,590 and M$_w$=3,060 and the product had M$_n$=5,090 and M$_w$=8,470.

Infrared absorption spectrum: in addition to absorptions originating with the polydimethylsiloxane, absorptions at 3310 cm$^1$ (N—H), 1632 cm$^1$ (C=O), and 1545 cm$^{-1}$ (amide II) were observed.

$^1$H NMR (CDCl$_3$, ppm): −0.04–0.16 (136H, m), 1.01 (3H, d), 1.05 (1H, m), 3.45 (1H, m), 3.54 (1H, m), 6.38 (1H, br), 7.78 (4H, s).

EXAMPLE 16

Reaction of 1,3,5-tris(azaoxasilacyclohexenyl)benzene and Alpha, Omega-polysiloxanediol 3.2 parts alpha, omega-polydimethylsiloxanediol (number-average molecular weight M$_n$=1,590) was slowly added dropwise to 1 part 1,3,5-tris(azaoxasilacyclohexenyl)benzene dissolved in 10 parts tetrahydrofuran. The polysiloxane gelled immediately. Removal of the tetrahydrofuran in a vacuum gave a residue of insoluble siloxane gel.

Infrared absorption spectrum: in addition to absorptions originating with the polydimethylsiloxane, absorptions at 3310 cm$^{-1}$ (N—H), 1638 cm$^{-2}$ (C=O), and 1561 cm$^{-1}$ (amide II) were observed.

NMR analysis could not be carried out because the sample was insoluble in chloroform.

That which is claimed is:

1. A 1-aza-3-oxa-4-silacyclohex-1-ene compound selected from the group consisting of those having the general formula (I) and tautomers thereof

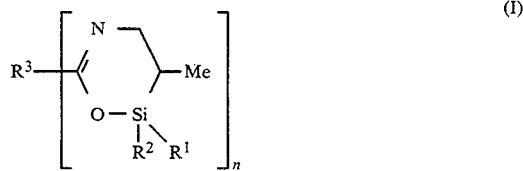
(I)

wherein R$^1$ and R$^2$ each independently denotes a monovalent organic group having 1 to 6 carbon atoms selected from the group consisting of saturated hydrocarbon groups and unsaturated hydrocarbon groups, R$^3$ denotes an organic group having 1 to 30 carbon atoms selected from the group consisting of saturated hydrocarbon groups and unsaturated hydrocarbon groups, said R$^3$ groups optionally containing a heteroatom selected from the group consisting of oxygen, nitrogen, sulfur, silicon, fluorine, chlorine, bromine and iodine, Me denotes a methyl radical and n is an integer having a value of 1 to 4.

2. The 1-aza-3-oxa-4-silacyclohex-1-ene compound of claim 1, in which R$^3$ is an aryl group which optionally contains a heteroatom selected from the group consisting of oxygen, nitrogen, sulfur, silicon, fluorine, chlorine, bromine and iodine.

3. The 1-aza-3-oxa-4-silacyclohex-1-ene compound according to claim 2 which is selected from the group consisting of the structures

(II)

-continued $$Q-\langle\bigcirc\rangle-Q \quad \text{(III)}$$

and $$\begin{array}{c} Q \\ Q-\langle\bigcirc\rangle \\ Q \end{array} \quad \text{(IV)}$$

wherein Q has the formula $$Q = -\left\langle\bigcirc\right\rangle-Me$$
with $O-Si$ bearing $R^2, R^1$ above Si, and $N-CH_2$ below in which $R^1$ and $R^2$ each independently denotes a monovalent organic group having 1 to 6 carbon atoms selected from the group consisting of saturated hydrocarbon groups and unsaturated hydrocarbon groups and Me denotes a methyl radical.

4. The 1-aza-3-oxa-4-silacyclohex-1-ene compound of claim 1, wherein n=1.

5. A method for introducing a functional group selected from the group consisting of the following formulas, and tautomers thereof, $$\begin{array}{c} Q \\ \langle\bigcirc\rangle \\ Q \end{array}$$

$$Q-\langle\bigcirc\rangle-Q$$

and $$\begin{array}{c} Q \\ Q-\langle\bigcirc\rangle \\ Q \end{array}$$

wherein Q has the formula $$Q = -\left\langle\bigcirc\right\rangle-Me$$

in which $R^1$ and $R^2$ each independently denotes a monovalent organic group having 1 to 6 carbon atoms selected from the group consisting of saturated hydrox-carbon groups and unsaturated hydrocarbon groups and Me denotes a methyl radical, into a hydroxyl-containing substance selected from the group consisting of hydroxyl-containing organic substances and hydroxyl-containing inorganic substances, said method comprising reacting said hydroxyl-containing substance with the compound of claim 3.

6. The method according to claim 5, wherein said hydroxyl-containing substance is selected from the group consisting of silanol-containing organic compounds, silanol-containing polymers and silanol-containing inorganic substances.

7. A method for introducing a group having the formula $$R^3C(O)-NH-CH_2CH(Me)-Si(R^1)(R^2)-O-$$

in which $R^1$ and $R^2$ each independently denotes a monovalent organic group having 1 to 6 carbon atoms selected from the group consisting of saturated hydrocarbon groups and unsaturated hydrocarbon groups, $R^3$ denotes an organic group having 1 to 30 carbon atoms selected from the group consisting of saturated hydrocarbon groups and unsaturated hydrocarbon groups, said $R^3$ groups optionally containing a heteroatom selected from the group consisting of oxygen, nitrogen, sulfur, silicon, fluorine, chlorine, bromine and iodine and Me denotes a methyl radical, into a hydroxyl-containing substance selected from the group consisting of hydroxyl-containing organic substances and hydroxyl-containing inorganic substances, said method comprising reacting said hydroxyl-containing substance with the compound of claim 4.

8. The method according to claim 7, wherein said hydroxyl-containing substance is selected from the group consisting of silanol-containing organic compounds, silanol-containing polymers and silanol-containing inorganic substances.

9. A method for crosslinking a hydroxyl-containing substance comprising reacting said hydroxyl-containing substance, in the presence or absence of water, with the compound of claim 3.

10. The method according to claim 9, wherein the hydroxyl-containing substance is a silanol-containing organic compound, silanol-containing polymer, or silanol-containing inorganic substance.

11. A method for the preparation of the 1-aza-3-oxa-4-silacyclohex-1-ene compound of claim 1, comprising reacting a 1-aza-2-silacyclobutane compound with the following general formula (V)

$$HR^1R^2Si-N\begin{array}{c}\diagup\diagdown\\ \diagdown\diagup\end{array}Me \quad \text{(V)}$$
with Si bearing $R^2, R^1$ with a carbonyl compound with the following general formula (VI)

$$R^3\left[\begin{array}{c}X\\ \|\\ O\end{array}\right]_n \quad \text{(VI)}$$

wherein $R^1$ and $R^2$ each independently denotes a monovalent organic group having 1 to 6 carbon atoms selected from the group consisting of saturated hydrocarbon groups and unsaturated hydrocarbon groups, $R^3$ denotes an organic group having 1 to 30 carbon atoms selected from the group consisting of saturated hydrocarbon groups and unsaturated hydrocarbon groups, said $R^3$ groups optionally containing a heteroatom selected from the group consisting of oxygen, nitrogen, sulfur, silicon, fluorine, chlorine, bromine and iodine, Me denotes a methyl radical, n is an integer having a value of 1 to 4 and X is selected from the group consisting of chlorine, bromine and acyloxy group of the formula $OC(=O)R^4$ in which $R^4$ is selected from the group consisting of $C_1$ to $C_{30}$ saturated hydrocarbon groups and unsaturated hydrocarbon groups which may optionally contain a heteroatom selected from the group consisting of nitrogen, oxygen, sulfur, silicon, fluorine, chlorine, bromine and iodine.

* * * * *